United States Patent [19]
Hayashida et al.

[11] Patent Number: 5,705,611
[45] Date of Patent: Jan. 6, 1998

[54] HUMAN GM-CSF RECEPTOR COMPONENT

[75] Inventors: Kazuhiro Hayashida, Karatsu, Japan; Toshio Kitamura; Atsushi Miyajima, both of Palo Alto, Calif.

[73] Assignee: Schering Corporation, Kenilworth, N.J.

[21] Appl. No.: 960,389

[22] PCT Filed: Jun. 16, 1991

[86] PCT No.: PCT/US91/04846

§ 371 Date: Jan. 7, 1993

§ 102(e) Date: Jan. 7, 1993

Related U.S. Application Data

[63] Continuation of Ser. No. 554,745, Jul. 18, 1990, Pat. No. 5,112,691.

[51] Int. Cl.$^6$ .................... C07K 14/705; C12N 15/12
[52] U.S. Cl. .................... 530/350; 435/69.1; 536/23.5
[58] Field of Search .................... 435/69.1; 530/350; 536/23.5

[56] References Cited

PUBLICATIONS

Clark et al., *Science*, vol. 236, pp.1229–1237, 1989.
Gearing et al., *The EMBO Journal*, vol. 8, No. 12, pp. 3667–3676, 1989.
Morstyn et al., *Cancer Investigation*, vol. 7, pp. 443–456, 1989.
Sachs, *Science*, vol. 238, pp. 1374–1379, 1987.
Young et al., *Blood*, vol. 68, pp. 1178–1181, 1986.
Hyashida et al., *Proc. Natl. Acad. Sci. USA*, 87 (Dec. 1990), 9655–9659.
Kitamura et al., *Proc. Natl. Acad. Sci. USA*, 88 (Jun. 1991), 5082–5086.

*Primary Examiner*—John Ulm
*Attorney, Agent, or Firm*—John H.C. Blasdale; Edwin P. Ching; Sheela Mohan-Peterson

[57] ABSTRACT

Nucleic acids encoding the β-chain of the human granulocyte-macrophage colony stimulating factor (GM-CSF) receptor, as well as the β-chain itself, are provided. The β-chain may be expressed with the α-chain in cellular hosts to form compositions useful in screening agonists and antagonists of human GM-CSF.

26 Claims, 3 Drawing Sheets

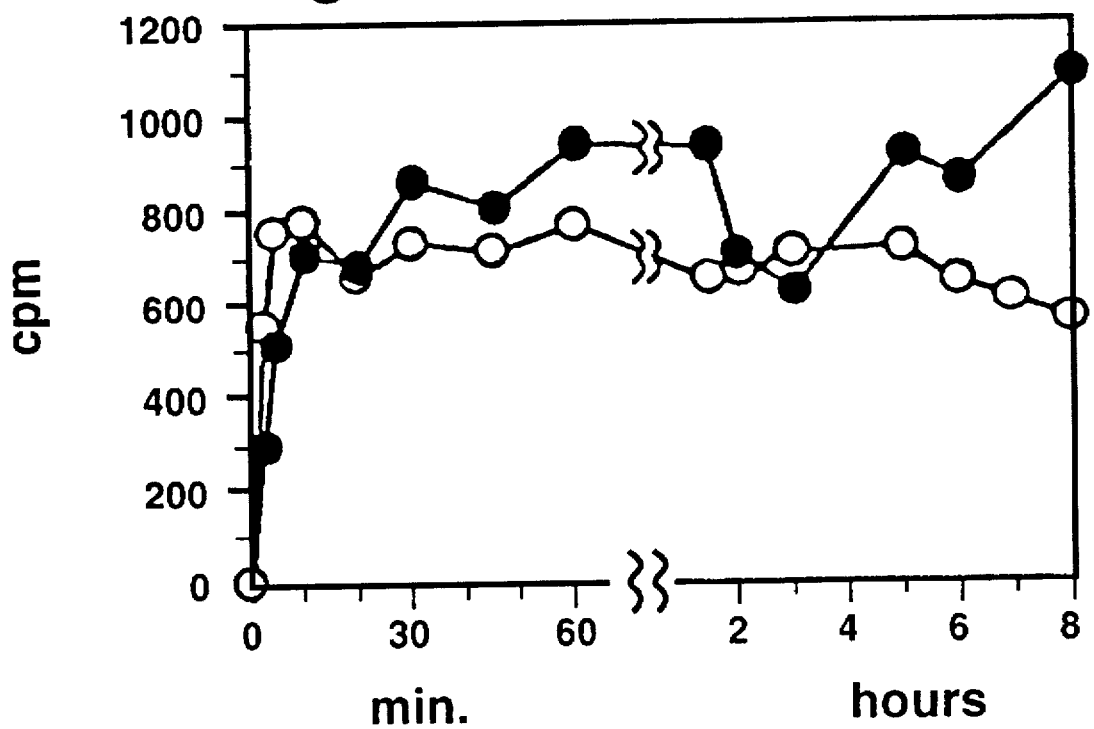
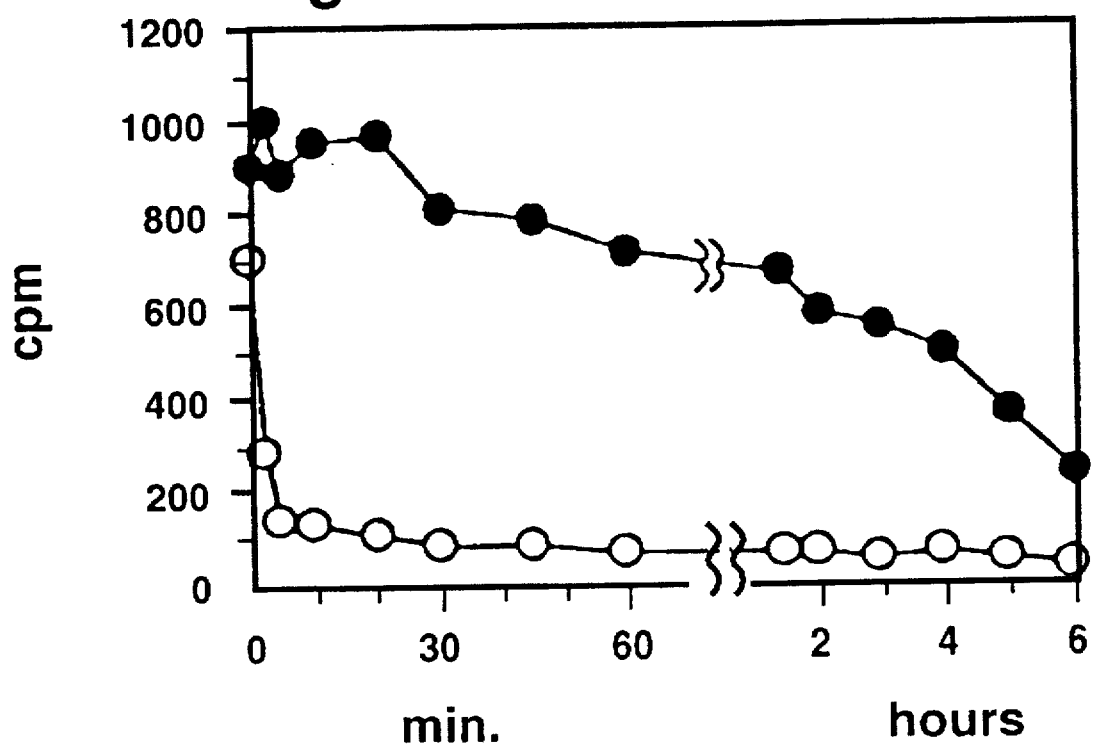

HUMAN GM-CSF RECEPTOR COMPONENT

The present application is the United States national application corresponding to International Application No. PCT/US91/04846 filed Jul. 16, 1991 and designating the United States, which PCT application is in turn a continuation of U.S. Application Ser. No. 07/554,745, filed 18 Jul. of 1990, now U.S. Pat. No. 5,112,691, the benefit of which applications are claimed pursuant to the provisions of 35 U.S.C. §§120, 363 and 365 (C).

FIELD OF THE INVENTION

The invention relates generally to the human granulocyte-macrophage colony stimulating factor (GM-CSF) receptor, and more particularly, to the synthesis of a human GM-CSF receptor component and to the use of the receptor component for screening agonists and antagonists of human GM-CSF.

BACKGROUND

Circulating blood cells are constantly replaced by newly developed cells. Replacement blood cells are formed in a process termed hematopoiesis which involves the production of at least eight mature blood cell types within two major lineages: (1) the myeloid lineage which includes red blood cells (erythrocytes), macrophages (monocytes), eosinophilic granulocytes, megakaryocytes (platelets), neutrophilic granulocytes, basophilic granulocytes (mast cells); and (2) the lymphoid lineage which includes T lymphocytes and B lymphocytes [Burgess and Nicola, Growth Factors and Stem Cells (Academic Press, New York, 1983)]. Much of the control of blood-cell formation is mediated by a group of interacting glycoproteins termed colony stimulating factors (CSFs). These glycoproteins are so named because of the in vivo and in vitro assays used to detect their presence. Techniques for the clonal culture of hematopoietic cells in semisolid culture medium have been especially important in the development of in vitro assays. In such cultures, individual progenitor cells (i.e., cells developmentally committed to a particular lineage, but still capable of proliferation) are able to proliferate to form a colony of maturing progeny in a manner which is believed to be essentially identical to the comparable process in vivo. The role of CSFs in hematopoiesis is the subject of many reviews, and is of great interest to clinical investigators who must treat blood diseases or deficiencies; e.g. Metcalf, The Hemopoietic Colony Stimulating Factors (Elsevier, N.Y., 1984); Clark and Kamen, Science, Vol. 236, pgs. 1229–1237 (1987); Sachs, Science, Vol. 238, pgs. 1374–1379 (1987); Dexter et al., eds., Colony Stimulating Factors (Dekker, N.Y., 1990); and Morstyn et al., Cancer Investigation, Vol. 7, pgs. 443–456 (1989).

CSFs are believed to play a role in the development and progression of myeloid leukemias; e.g., Metcalf, Hamatol, Bluttransfus., Vol. 31, pgs. 16–25 (1987). Myeloid leukemias are clonal neoplasms of granulocyte-macrophage precursor cells, which fall into two major groups: chronic myeloid leukemia (CML) and acute myeloid leukemia (AML). CML is characterized by expansion in the marrow of the granulocyte-monocyte population at all stages of maturation, with massive enlargement of hematopoietic populations in the spleen and blood. Whereas chemotherapy is successful in reducing the excessive size of the leukemic cell populations, conventional regimens have not succeeded in preventing terminal acute transformation (of progressively higher proportions of cells into immature or abnormal forms) or in extending the life spans of afflicted patients (Metcalf, cited above, 1984). AML is characterized by an accumulation of immature granulocyte-monocyte blast cells with often little or no evidence of maturing granulocyte-monocyte cells. The disease primarily involves the bone marrow, and spleen enlargement usually is only moderate. Total blood nucleated cells may or may not be elevated, but there is a high proportion of immature blast cells associated with relatively few mature cells. There is usually an associated anemia, thrombocytopenia and a relative absence in the marrow and peripheral blood of mature granulocytes and monocytes. Death usually results from uncontrollable hemorrhage or overwhelming infections (Metcalf, cited above, 1984).

It is believed that both forms of leukemia are driven by abnormal production of, or responsiveness to, colony stimulating factors, particularly GM-CSF. In particular, it has been shown that leukemic cells from some AML patients are capable of autonomous proliferation in vitro because they express GM-CSF constitutively, and that such autonomous proliferation can be inhibited by the addition of GM-CSF neutralizing antiserum [Young et al., Blood, Vol. 68, pgs. 1178–1181 (1986)]. It is believed that myeloid leukemias, in particular AML, may be treated by blocking the ability of GM-CSF to stimulate cell growth.

Recently, a low-affinity receptor of human GM-CSF, referred to herein as the α-chain, has been cloned and characterized [Gearing et at., EMBO J. Vol. 8, pgs. 3667–3676 (1989)]. The availability of a high affinity human GM-CSF receptor would provide a valuable tool for screening candidate GM-CSF agonists and antagonists.

SUMMARY OF THE INVENTION

The invention is directed to a component of the human GM-CSF receptor, referred to herein as the β-chain of the human GM-CSF receptor, and to compositions thereof which bind with high affinity to human GM-CSF. The invention includes allelic and genetically engineered variants of the β-chain receptor and nucleic acids encoding the β-chain receptor and its allelic and genetically engineered variants. Preferably, the receptor component of the invention is selected from the group of polypeptides of the open reading frame defined by the amino acid sequence given in SEQ ID NO. 2.

Most preferably, the receptor component of the invention is defined by the amino acid sequence given in SEQ ID NO 2 but lacking the signal sequence.

Although the Formula given in SEQ ID NO. 2, with or without the leader sequence, includes the intracellular domain of the β-chain of the receptor, it is clear that a truncated sequence (with or without the leader sequence) that retains its extracellular and transmembrane domains and its ability of operably associating with the α-chain falls within the concept of the invention.

The invention is based in part on the discovery and cloning of cDNAs which are capable of expressing proteins that bind to human GM-CSF with high affinity. One such clone, designated pKH97, was deposited with the American Type Culture Collection (ATCC) (Rockville, Md.) under accession number 40847 on Jul. 17th 1990. The invention includes nucleic acids (i) that are effectively homologous to the cDNA insert of pKH97, and (ii) that encode proteins that form high affinity GM-CSF receptors in association with the low affinity α-chain receptor protein, e.g. as encoded by pKH125, also deposited with the ATCC under accession number 40848 on Jul. 17th 1990. As used herein, high affinity in reference to GM-CSF receptor binding means that GM-CSF binds to the associated α- and β-chains of the receptor with a binding constant that is at least an order of magnitude less than that for binding to either component alone. More preferably, high affinity means that GM-CSF binds to the associated α- and β-chains of the receptor with a binding constant, $K_d$, less than 1 nM; and most preferably, less than 200 pM.

BRIEF DESCRIPTION OF THE DRAWINGS

FIG. 2A illustrates the association rate of $^{125}$I-labeled human GM-CSF to the NIH3T3 stable transfectants.

FIG. 2B illustrates the dissociation rate of $^{125}$I-labeled human GM-CSF to the NIH3T3 stable transfectants.

DETAILED DESCRIPTION OF THE INVENTION

Figure 1A:
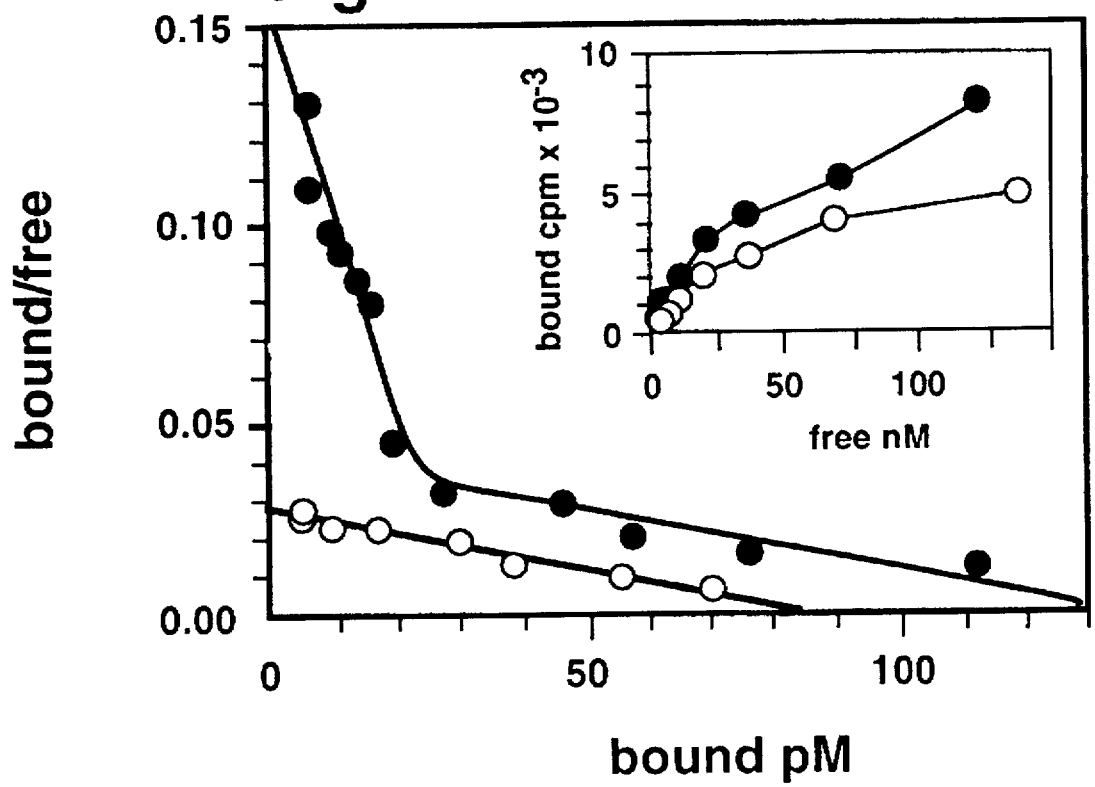
FIG. 1A illustrates the binding of $^{125}$I-labeled human GM-CSF to COS 7 cells transiently co-transfected with KH97 and pKH125.

I. Obtaining and Expressing cDNAs for the β-Chain of the Human GM-CSF Receptor

The term "effectively homologous" as used herein means that the nucleotide sequence is capable of being detected by a hybridization probe derived from a cDNA clone of the invention. The exact numerical measure of homology necessary to detect nucleic acids coding for a receptor β-chain depends on several factors including (1) the homology of the probe to non-β-chain coding sequences associated with the target nucleic acids, (2) the stringency of the hybridization conditions, (3) whether single stranded or double stranded probes are employed, (4) whether RNA or DNA probes are employed, (5) the measures taken to reduce nonspecific binding of the probe, (6) the nature of the method used to label the probe, (7) the fraction of guanidine and cytosine bases in the probe, (8) the distribution of mismatches between probe and target, (9) the size of the probe, and the like. Preferably, an effectively homologous nucleic acid sequence is at least seventy percent (70%) homologous to the cDNA of the invention. More preferably, an effectively homologous nucleic acid is at least ninety percent (90%) homologous to the cDNA of the invention. Most particularly, an effectively homologous nucleic acid sequence is one whose cDNA can be isolated by a probe based on the nucleic acid sequence of SEQ ID NO. 1 using a standard hybridization protocol with no more than a few false positive signals, e.g. fewer than a hundred. There is an extensive literature that provides guidance in selecting conditions for such hybridizations: e.g., Hames et al., Nucleic Acid Hybridization: A Practical Approach (IRL Press, Washington, D.C., 1985); Gray et al., *Proc. Natl. Acad. Sci.*, Vol. 80, pgs. 5842–5846 (1983); Kafatos et al., *Nucleic Acids Research*, Vol. 7, pgs. 1541–1552 (1979); and Williams, *Genetic Engineering*, Vol. 1, pgs. 1–59 (1981), to name a few. By way of example, the nucleic acid of SEQ ID NO. 1 can be used as a probe in colony hybridization assays as described by Benton and Davis, *Science*, Vol. 196, pg. 180 (1977). Preferably, low stringency conditions are employed for the probe employed. (The dissociation temperature depends on the probe length.) For example, for a probe of about 20–40 bases a typical prehybridization, hybridization, and wash protocol is as follows: (1) prehybridization: incubate nitrocellulose filters containing the denatured target DNA for 3–4 hours at 55° C. in 5x Denhardt's solution, 5x SSPE (20x SSPE consists of 174 g NaCl, 27.6 g $NaH_2PO_4.H_2O$, and 7.4 g EDTA in 800 ml $H_2O$ adjusted to pH 7.4 with 10N NaOH), 0.1% SDS, and 100 µg/ml denatured salmon sperm DNA, (2) hybridization: incubate filters in prehybridization solution plus probe at 55° C. for 2 hours, (3) wash: three 15 minute washes in 300–500 ml volumes of 6x SSC and 0.1% SDS at room temperature, followed by a final 1–1.5 minute wash in 300–500 ml of 1x SSC and 0.1% SDS at 55° C. Other equivalent procedures, e.g. employing organic solvents such as formamide, are well known in the art.

Homology as the term is used herein is a measure of similarity between two nucleotide (or amino acid) sequences. Homology is expressed as the fraction or percentage of matching bases (or amino acids) after two sequences (possibly of unequal length) have been aligned. The term alignment is used in the sense defined by Sankoff and Kruskal in chapter one of Time Warps, String Edits, and Macromolecules: The Theory and Practice of Sequence Comparison (Addison-Wesley, Reading, Mass., 1983). Roughly, two sequences are aligned by maximizing the number of matching bases (or amino acids) between the two sequences with the insertion of a minimal number of "blank" or "null" bases into either sequence to bring about the maximum overlap. Given two sequences, algorithms are available for computing their homology: e.g., Needleham and Wunsch, *J. Mol. Biol.*, Vol. 48, pgs. 443–453 (1970); and Sankoff and Kruskal (cited above), pgs. 23–29. Also, commercial services and software packages are available for performing such comparisons, e.g. Intelligenetics, Inc. (Mountain View, Calif.), and University of Wisconsin Genetics Computer Group (Madison, Wis.).

Probes based on the nucleic acid sequence of SEQ ID NO. 3 can be synthesized on commercially available DNA synthesizers, e.g. Applied Biosystems model 381A, using standard techniques, e.g. Gait, Oligonucleotide Synthesis: A Practical Approach, (IRL Press, Washington D.C., 1984). It is preferable that the probe be at least 18–30 bases long. More preferably, the probe is at least 100–200 bases long. Probes of the invention can be labeled in a variety of ways standard in the art, e.g. with radioactive labels [Berent et al., *Biotechniques*, pgs. 208–220 (May/June 1985); Meinkoth et al., *Anal. Biochem*, Vol. 138, pgs. 267–284 (1984); Szostak et al., *Meth, Enzymol.*, Vol. 68, pgs. 419–429 (1979); and the like], or with non-radioactive labels [Chu et al., *DNA*, Vol. 4, pgs. 327–331 (1985); Jablonski et al., *Nucleic Acids Research*. Vol. 14, pgs. 6115–6128 (1986); and the like].

Hybridization probes can also be used to screen candidate sources of β-chain mRNA prior to library construction, e.g. by RNA blotting: Maniatis et al., Molecular Cloning: A Laboratory Manual, pgs. 202–203 (Cold Spring Harbor Laboratory, N.Y., 1982); or Hames and Higgins, eds., pgs. 139–143 in Nucleic Acids Hybridization (IRL Press, Washington, D.C., 1985). Sources of mRNA encoding the desired polypeptides include cell populations or cell lines that express, or can be induced to express, large numbers of GM-CSF receptors on their surfaces, e.g. in excess of 3000–5000.

Preferably, the α- and β-chains of the GM-CSF receptor are co-transfected into a mammalian expression system (i.e. host-expression vector combination). Many reviews are available which provide guidance for making choices and/or modifications of specific mammalian expression systems: e.g. (to name a few), Kucherlapati et al., *Critical Reviews in Biochemistry*, Vol. 16, Issue 4, pgs. 349–379 (1984), and Banerji et at., *Genetic Engineering*, Vol. 5, pgs. 19–31 (1983), review methods for transfecting and transforming mammalian cells; Reznikoff and Gold, eds., Maximizing Gene Expression (Butterworths, Boston, 1986) review selected topics in gene expression in *E. coli*, yeast, and mammalian cells; and Thilly, Mammalian Cell Technology (Butterworths, Boston, 1986) reviews mammalian expression systems. Likewise, many reviews are available which describe techniques and conditions for linking and/or manipulating specific cDNAs and expression control sequences to create and/or modify expression vectors suitable for use with the present invention; e.g. Maniatis et al., Molecular Cloning: A Laboratory Manual (Cold Spring Harbor Laboratory, N.Y., 1982); Glover, DNA Cloning: A Practical Approach, Vol. I and II (IRL Press, Oxford, 1985), and Perbal, A Practical Guide to Molecular Cloning (John Wiley & Sons, N.Y., 1984), to name only a few.

Several DNA tumor viruses have been used as vectors for mammalian hosts. Particularly important are the numerous vectors which comprise SV40 replication, transcription, and/or translation control sequences coupled to bacterial replication control sequences; e.g., the pcD vectors developed by Okayama and Berg, disclosed in *Mol. Cell. Biol.*, Vol. 2, pgs. 161–170 (1982) and *Mol. Cell. Biol.*, Vol. 3, pgs. 280–289 (1983), both of which are incorporated herein by reference; the SV40 vectors disclosed by Hamer in *Genetic Engineering*, Vol. 2, pgs. 83–100 (1980), and U.S. Pat. No. 4,599,308, both of which are incorporated herein by reference; and the vectors additionally containing adenovirus regulatory elements, disclosed by Kaufman and Sharp, in *Mol. Cell. Biol.*, Vol. 2, pgs. 1304–1319 (1982), and by Clark et at. in U.S. Pat. No. 4,675,285, both of which are incorporated herein by reference. COS7 monkey cells, described by Gluzman, *Cell*, Vol. 23, pgs. 175–182 (1981) and available from the ATCC (accession no. CRL 1651), are usually the preferred hosts for the above vectors. SV40-based vectors suitable for mammalian receptor expression have been developed by Aruffo and Seed [*Proc. Natl. Acad. Sci.*, Vol. 84, pgs. 3365–3369 and 8573–8577 (1987)].

II. Binding Assays

Binding assays are accomplished by letting a ligand of unknown specificity or affinity compete with a known amount or concentration of labeled human GM-CSF for receptor binding sites of a sample of cells transfected or transformed with pKH97 and pKH125, or their equivalents. Preferably, the GM-CSF is labeled by radioiodination using standard protocols, e.g. reaction with 1,3,4,6-tetrachloro-3α, 6α-diphenylglycouril described by Fraker et al., *Biochem Biophys. Res. Commun.*, Vol. 80, pgs. 849–857 (1978) (and available from Pierce Chemical Co. as Iodogen). Generally, the binding assay is conducted as described by Lowenthal et al., *J. Immunol.*, Vol 140, pgs. 456–464 (1988), which is incorporated by reference. Briefly, aliquots of cells are incubated in the presence of $^{125}$I-labeled human GM-CSF in a final volume of 200 µl culture medium in microfuge tubes at 4° C. Cell-bound $^{125}$I-labeled GM-CSF was separated from non-bound $^{125}$I-labeled GM-CSF by centrifugation through an oil gradient (10,000 x G for 2 min). Nonspecific binding is measured in the presence of a 100-fold excess of partially purified unlabeled human GM-CSF.

The following Examples serve to illustrate the invention but do not limit it in any way:

EXAMPLES

Example I

Construction of cDNA library from TF-1 cells and isolation of pKH97 and pKH125

Figure 3:
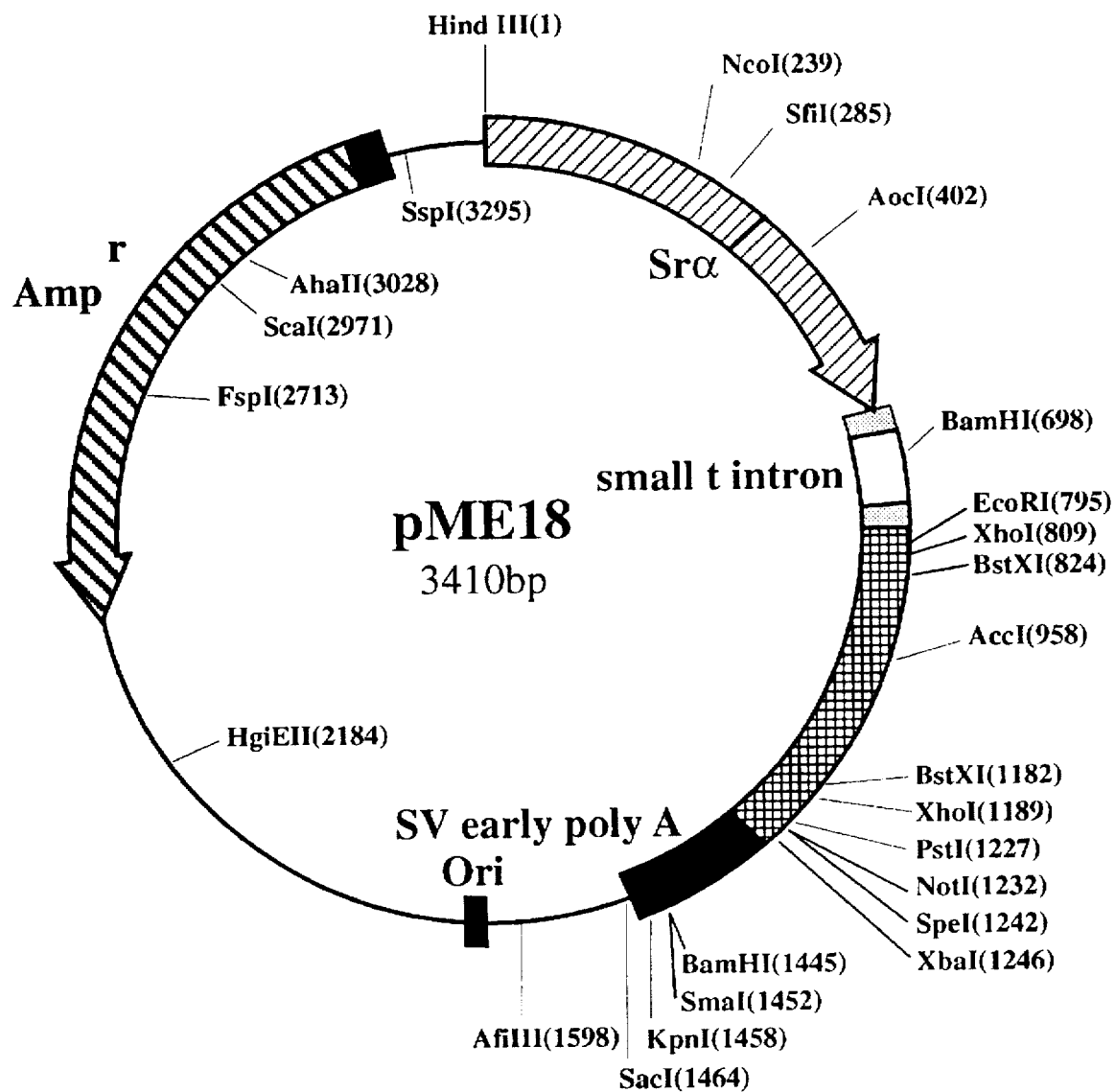
FIG. 3 is a restriction map of the vector pME18.

Poly(A)$^+$ RNA isolated from TF-1 cells (Kitamura et al., *J. Cell. Physiol.*, Vol. 140, pgs. 323–334 (1989)) by the guanidium isothiocyanate method (Chirgwin et al., *Biochemistry*, Vol. 18, pgs. 5294–5299 (1978)) was converted to double-stranded cDNA using oligo-(dT) primers. After BstXI linkers were ligated to both ends of the cDNAs, the cDNAs were digested with XbaI (the 3'-region fortuitously containing a unique XbaI site) and re-cloned into BstXI/XbaI-digested pME18, an SV40-based mammalian expression vector (see FIG. 3). pKH97 was isolated by using probes constructed from initially isolated truncated cDNAs. The truncated cDNAs were isolated using a $^{32}$P-labeled mouse interleukin-3 receptor cDNA fragment (described by Itoh et al., *Science*, Vol. 247, pgs. 324–334 (1990)) as a hybridization probe under low stringency conditions (hybridization at 42° C. with 6xSSPE in the presence of 20% formamide and washing at 50° C. with 2xSSPE). pKH97 was transfected into COS 7 cells by a standard protocol, e.g. as described by Yokota et at., *Proc. Natl. Acad. Sci.*, Vol. 84, pgs. 7388–7392 (1987) (5 µg of plasmid DNA were transfected into semi-confluent COS 7 cells by the DEAE-dextran method; 72 hours after transfection, the cells were harvested for binding assays, using iodinated cytokines as described below). No specific binding was displayed by any of the following human cytokines at the following concentrations: IL-2 (1 nM), IL-3 (20 nM), IL-4 (1 nM), IL-5 (5 nM), GM-CSF (20 nM), and EPO (10 nM).

A cDNA encoding the α-chain of the human GM-CSF receptor was isolated from the same library using the polymerase chain reaction with specific oligonucleotide primers corresponding to the 5'-untranslated and the 3'-untranslated regions of the cDNA described by Gearing et al., *EMBO J.*, Vol. 8, pgs. 3667–3676 (1989). Inserting the isolated cDNA into pME18 gave pKH125.

Example II

Co-transfection of pKH97 and pKH125 into COS 7 cells

A total of 5 µg of equal amounts of pKH97 and pKH125 plasmid DNA was transfected into semi-confluent COS 7 cells by the DEAE-dextran method. 72 hours after transfection, the cells were harvested and analyzed in GM-CSF binding assays. Duplicates of 2×10$^5$ COS 7 cells in 0.1 ml of RPMI 1640 containing 10% fetal calf serum, 2 mM EDTA, 0.02% sodium azide and 20 mM Hepes (pH 7.4) were incubated for 3 hours at 4° C. with various concentrations of $^{125}$I-labeled human GM-CSF with or without an excess amount of non-labeled human GM-CSF. The cell-bound radioactivity was measured by separating the cells from free ligand by centrifugation through an oil layer, as described by Schreurs et at., Growth Factors, Vol. 2, pgs. 221–233 (1990). GM-CSF was iodinated by a standard protocol [Chiba et al., *Leukemia*, Vol. 4, pgs. 22–36 (1990)]. Briefly, 5 µg of *E. coli*-produced human GM-CSF was incubated in 30–50 µl of 50 mM sodium borate buffer (pH 8.0) with 1 mCi of the dried Bolton-Hunter reagent for 12–16 hours at 4° C. Glycine was added to 2.5 mg/ml to stop the reaction and the iodinated GM-CSF was separated from the free Bolton-Hunter reagent by a PD-10 column. The iodinated human GM-CSF had a specific radioactivity of (4–8)×10$^7$ cpm/µg and was stable for about two months in Hepes-buffered Hank's balanced salt solution containing 0.1% gelatin, 0.1% bovine serum albumin, and 0.02% sodium azide.

FIG. 1A shows the receptor binding data. Open circles correspond to COS 7 cells (controls) transfected with pKH125 and pME18 (same vector as pKH97, but without the cDNA insert). Closed circles correspond to COS 7 cells transfected with pKH125 and pKH97. The Scatchard plots of the binding data are shown. The inserted graphs show equilibrium binding profiles. As can be seen from the data, both high ($K_d$=120 pM) and low ($K_d$=6.6 nM) affinity binding sites are indicated (the $K_d$ values being computed by the LIGAND program, De Lean et al., *Mol. Pharmacol.*, Vol. 21, pgs. 5–16 (1982)).

Example III

Co-transfection of pKH97 and pKH125 into NIH3T3 Cells

Figure 1B:
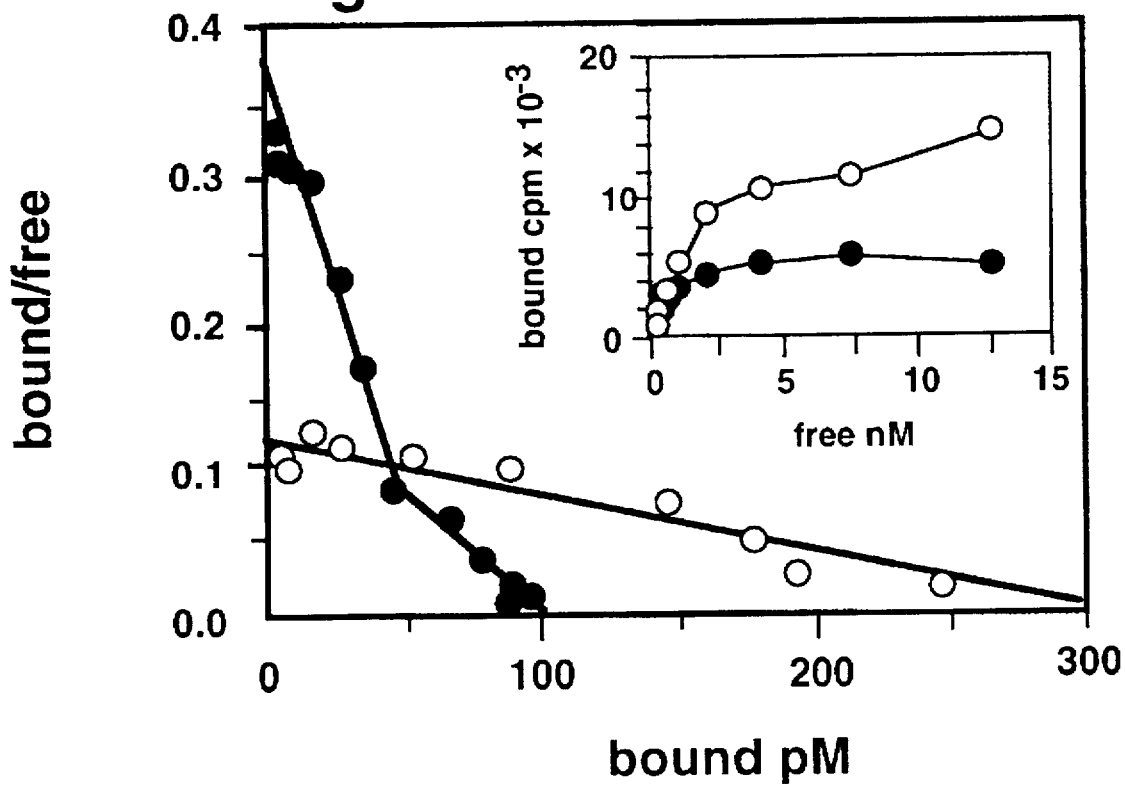
FIG. 1B illustrates the binding of $^{125}$I-labeled human GM-CSF to NIH3T3 cells stably transfected with KH97 and pKH125.

A DNA fragment containing the neomycin-resistance gene, neo, was inserted into pKH97 to form pKH97neo. NIH3T3 cells were stably transfected with pKH97neo and pKH125 by the calcium-phosphate procedure, described by Chen and Okayama, *Mol. Cell. Biol.*, Vol. 7, pgs. 2745–2752 (1987), which reference is incorporated by reference. Stable transfectants were selected by 1 mg/ml of G418. FIG. 1B shows the binding data for the transfected NIH3T3 cells. The open circles correspond to control NIH3T3 cells transfected with pKH97neo and pME18. Closed circles correspond to NIH3T3 cells transfected with pKH97neo and pKH125. The latter displayed high affinity binding with a $K_d$ of 170 pM. Labeled GM-CSF association-and dissociation rates were also examined in the transfected NIH3T3 cells. FIGS. 2A and 2B illustrate the data. Open circles correspond to NIH3T3 cells expressing only the α-chain. Closed circles correspond to NIH3T3 cells expressing both the α-chain and β-chain of the GM-CSF receptor. The latter displayed a much slower rate of dissociation ($T_{1/2}$=2 min versus $T_{1/2}$=360 min).

Example IV

Use of Co-transfected COS 7 cells to screen for GM-CSF Antagonists

Aliquots of COS 7 cells co-transfected with pKH97 and pKH125 as described above are distributed to wells of microtiter plates in 200 μl of medium containing $^{125}$I-labeled human GM-CSF at concentrations of 100 pM, 500 pM, and 1 nM. 100 μl samples of microbial supernatants free of cells are added to the transfected COS 7 cells at each of the different concentrations of $^{125}$I-labeled GM-CSF. After incubating for 3 hours the COS 7 cells are harvested and assayed for bound radioactivity. COS 7 cells with low counts of bound radioactivity correspond to microbial samples containing candidate antagonists or agonists of human GM-CSF.

The 'stuffer' region of the vector pME18 is described by Seed et al., *Proc. Natl. Acad. Sci.*, Vol. 84 (1987), pp. 3365–3369.

On Jul. 17th 1990, Applicants deposited pKH97 and pKH125 with the American Type Culture Collection, Rockville, Md., USA (ATCC), under accession numbers 40847 and 40848, respectively. These deposits were made for international purposes under the Budapest Treaty, and also for US purposes under conditions as provided under the ATCC's agreement for Culture Deposit for Patent Purposes, which assures that the deposits will be made available to the US Commissioner of Patents and Trademarks pursuant to 35 USC 122 and 37 CFR 1.14, and will be made available to the public upon issue of a U.S. patent, which requires that the deposit be maintained. Availability of the deposited plasmids is not to be construed as a license to practise the invention in contravention of the rights granted under the authority of any government in accordance with its patent laws.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to best utilize the invention in various embodiments and with various modifications as are suited to the particular use contemplated. It is intended that the scope of the invention be defined by the claims appended hereto.

---

We claim:

1. A polypeptide substantially free of other non-receptor proteins comprising the extracellular and transmembrane domains of SEQ ID NO: 2.

2. The polypeptide of claim 1, which is capable of operable association with a human GM-CSF receptor α-chain to form a GM-CSF receptor.

3. The polypeptide of claim 2, wherein said receptor is capable of binding human GM-CSF with high affinity.

4. The polypeptide of claim 3, wherein said high affinity provides a binding constant at least an order of magnitude less than a binding constant of either said polypeptide or α-chain alone.

5. The polypeptide of claim 3 wherein said high affinity provides a binding constant of less than 1 nM.

6. The polypeptide of claim 3, wherein said high affinity provides a binding constant of less than 200 pM.

7. The polypeptide of claim 1 comprising residues 1 to 448 of SEQ ID NO: 2.

8. The polypeptide of claim 7, which further comprises amino residues of 449 to 880 of SEQ ID NO: 2.

9. The polypeptide of claim 1, substantially free of other human proteins.

10. A composition of matter comprising the polypeptide of claim 1 in operable association with an α-chain, thereby forming a receptor which binds GM-CSF with high affinity.

11. The composition of claim 10, which exhibits no specific binding to:

a) IL-2 at 1 nM;
   b) IL-3 at 20 nM;
   c) IL-4 at 1 nM;
   d) IL-5 at 5 nM; or
   e) EPO at 10 nM.

12. The polypeptide of claim 1 which is the mature form of the amino acid sequence of SEQ ID NO. 2.

13. The protein of claim 12 made in:

a) a mammalian cell;
   b) an E. coli cell; or
   c) a yeast cell.

14. The protein of claim 12, which is capable of operable association with a human GM-CSF receptor α-chain to bind GM-CSF with high affinity.

15. The protein of claim 14, wherein said high affinity provides a binding constant at least an order of magnitude less than a binding constant of either said polypeptide or α-chain alone.

16. The polypeptide of claim 14, wherein said high affinity provides a binding constant of less that 1 nM.

17. The polypeptide of claim 14, wherein said high affinity binding provides a binding constant of less that 200 pM.

18. A recombinant polypeptide comprising the extracellular and transmembrane domains of SEQ ID NO: 2.

19. The polypeptide of claim 18, wherein said polypeptide is expressed in:

a) a mammalian cell;
   b) an E. coli cell; or
   c) a yeast cell.

20. The recombinant polypeptide of claim 18, comprising residues 1 to 448 of SEQ ID NO: 2.

21. The recombinant polypeptide of claim 18 defined by the mature form of a GM-CSF receptor β-chain of SEQ ID NO: 2.

22. The polypeptide of claim 21, comprising residues 1 to 880 of SEQ ID NO: 2.

23. The recombinant polypeptide of claim 18, capable of operable association with an α-chain of a human GM-CSF receptor.

24. The recombinant polypeptide of claim 18, in operable association with an α-chain of a GM-CSF receptor.

25. The recombinant polypeptide of claim 24, wherein said operable association provides binding of human GM-CSF with high affinity.

26. The recombinant polypeptide of claim 25 wherein said high affinity provides a binding constant of less than 200 pM.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 3475 base pairs
        ( B ) TYPE: nucleotides
        ( C ) STRANDEDNESS: single
        ( D ) TOPOLOGY: linear ( v i ) ORIGINAL SOURCE:
        ( A ) ORGANISM: human ( i x ) FEATURE:
        ( D ) OTHER INFORMATION: DNA sequence encoding Human GM_CSF receptor ( x i ) SEQUENCE DESCRIPTION: SEQ ID NO: 1:

```
GAAGACTGGT   CTCTCCCACC   ACACAGAGGC   CTGGAGGAGG   CAGAGGCCAG   GAGGGAGAGG         60
```

| | | | | |
|---|---|---|---|---|
| TCCCAAGAGC | CTGTGAAATG | GGTCTGGCCT | GGCTCCCAGC | TGGGCAGGAA CACAGGACTT | 120 |
| CAGGACACTA | AGGACCCTGT | CATGCCCATG | GCCAGCACCC | ACCAGTGCTG GTGCCTGCCT | 180 |
| GTCCAGAGCT | GACCAGGGAG | ATG GTG CTG | GCC CAG GGG | CTG CTC TCC ATG GCC | 233 |
| CTG CTG GCC | CTG TGC TGG | GAG CGC AGC | CTG GCA GGG | GCA GAA GAA ACC | 281 |
| ATC CCG CTG | CAG ACC CTG | CGC TGC TAC | AAC GAC TAC | ACC AGC CAC ATC | 329 |
| ACC TGC AGG | TGG GCA GAC | ACC CAG GAT | GCC CAG CGG | CTC GTC AAC GTG | 377 |
| ACC CTC ATT | CGC CGG GTG | AAT GAG GAC | CTC CTG GAG | CCA GTG TCC TGT | 425 |
| GAC CTC AGT | GAT GAC ATG | CCC TGG TCA | GCC TGC CCC | CAT CCC CGC TGC | 473 |
| GTG CCC AGG | AGA TGT GTC | ATT CCC TGC | CAG AGT TTT | GTC GTC ACT GAC | 521 |
| GTT GAC TAC | TTC TCA TTC | CAA CCA GAC | AGG CCT CTG | GGC ACC GGC TC | 569 |
| ACC GTC ACT | CTG ACC CAG | CAT GTC CAG | CCT CCT GAG | CCC AGG GAC CTG | 617 |
| CAG ATC AGC | ACC GAC CAG | GAC CAC TTC | CTG CTG ACC | TGG AGT GTG GCC | 665 |
| CTT GGG AGT | CCC CAG AGC | CAC TGG TTG | TCC CCA GGG | GAT CTG GAG TTT | 713 |
| GAG GTG GTC | TAC AAG CGG | CTT CAG GAC | TCT TGG GAG | GAC GCA GCC ATC | 761 |
| CTC CTC TCC | AAC ACC TCC | CAG GCC ACC | CTG GGG CCA | GAG CAC CTC ATG | 809 |
| CCC AGC AGC | ACC TAC GTG | GCC CGA GTA | CGG ACC CGC | CTG GCC CCA GGT | 857 |
| TCT CGG CTC | TCA GGA CGT | CCC AGC AAG | TGG AGC CCA | GAG GTT TGC TGG | 905 |
| GAC TCC CAG | CCA GGG GAT | GAG GCC CAG | CCC CAG AAC | CTG GAG TGC TTC | 953 |
| TTT GAC GGG | GCC GCC GTG | CTC AGC TGC | TCC TGG GAG | GTG AGG AAG GAG | 1001 |
| GTG GCC AGC | TCG GTC TCC | TTT GGC CTA | TTC TAC AAG | CCC AGC CCA GAT | 1049 |
| GCA GGG GAG | GAA GAG TGC | TCC CCA GTG | CTG AGG GAG | GGG CTC GGC AGC | 1097 |
| CTC CAC ACC | AGG CAC ACC | TGC CAG ATT | CCC GTG CCC | GAC CCC GCG ACC | 1145 |
| CAC GGC CAA | TAC ATC GTC | TCT GTT CAG | CCA AGG AGG | GCA GAG AAA CAC | 1193 |
| ATA AAG AGC | TCA GTG AAC | ATC CAG ATG | GCC CCT CCA | TCC CTC AAC GTG | 1241 |
| ACC AAG GAT | GGA GAC AGC | TAC AGC CTG | CGC TGG GAA | ACA ATG AAA ATG | 1289 |
| CGA TAC GAA | CAC ATA GAC | CAC ACA TTT | GAG ATC CAG | TAC AGG AAA GAC | 1337 |
| ACG GCC ACG | TGG AAG GAC | AGC AAG ACC | GAG ACC CTC | CAG AAC GCC CAC | 1385 |
| AGC ATG GCC | CTG CCA GCC | CTG GAG CCC | TCC ACC AGG | TAC TGG GCC AGG | 1433 |
| GTG AGG GTC | AGG ACC TCC | CGC ACC GGC | TAC AAC GGG | ATC TGG AGC GAG | 1481 |
| TGG AGT GAG | GCG CGC TCC | TGG GAC ACC | GAG TCG GTG | CTG CCT ATG TGG | 1529 |
| GTG CTG GCC | CTC ATC GTG | ATC TTC CTC | ACC ACT GCT | GTG CTC CTG GCC | 1577 |
| CTC CGC TTC | TGT GGC ATC | TAC GGG TAC | AGG CTG CGC | AGA AAG TGG GAG | 1625 |
| GAG AAG ATC | CCC AAC CCC | AGC AAG AGC | CAC CTG TTC | CAG AAC GGG AGC | 1673 |
| GCA GAG CTT | TGG CCC CCA | GGC AGC ATG | TCG GCC TTC | ACT AGC GGG AGT | 1721 |
| CCC CCA CAC | CAG GGG CCG | TGG GGC AGC | GCC TTC CCT | GAG CTG GAG GGG | 1769 |
| GTG TTC CCT | GTA GGA TTC | GGG GAC AGC | GAG GTG TCA | CCT CTC ACC ATA | 1817 |
| GAG GAC CCC | AAG CAT GTC | TGT GAT CCA | CCA TCT GGG | CCT GAC ACG ACT | 1865 |
| CCA GCT GCC | TCA GAT CTA | CCC ACA GAG | CAG CCC CCC | AGC CCC CAG CCA | 1913 |
| GGC CCG CCT | GCC GCC TCC | CAC ACA CCT | GAG AAA CAG | GCT TCC AGC TTT | 1961 |
| GAC TTC AAT | GGG CCC TAC | CTG GGG CCG | CCC CAC AGC | CGC TCC CTA CCT | 2009 |

```
GAC ATC CTG GGC CAG CCG GAG CCC CCA CAG GAG GGT GGG AGC CAG AAG    2057
TCC CCA CCT CCA GGG TCC CTG GAG TAC CTG TGT CTG CCT GCT GGG GGG    2105
CAG GTG CAA CTG GTC CCT CTG GCC CAG GCG ATG GGA CCG GGA CAG GCC    2153
GTG GAA GTG GAG AGA AGG CCG AGC CAG GGG GCT GCA GGG AGT CCC TCC    2201
CTG GAG TCC GGG GGA GGC CCT GCC CCT CCT GCT CTT GGG CCA AGG GTG    2249
GGA GGA CAG GAC CAA AAG GAC AGC CCT GTG GCT ATA CCC ATG AGC TCT    2297
GGG GAC ACT GAG GAC CCT GGA GTG GCC TCT GGT TAT GTC TCC TCT GCA    2345
GAC CTG GTA TTC ACC CCA AAC TCA GGG GCC TCG TCT GTC TCC CTA GTT    2393
CCC TCT CTG GGC CTC CCC TCA GAC CAG ACC CCC AGC TTA TGT CCT GGG    2441
CTG GCC AGT GGA CCC CCT GGA GCC CCA GGC CCT GTG AAG TCA GGG TTT    2489
GAG GGC TAT GTG GAG CTC CCT CCA ATT GAG GGC CGG TCC CCC AGG TCA    2537
CCA AGG AAC AAT CCT GTC CCC CCT GAG GCC AAA AGC CCT GTC CTG AAC    2585
CCA GGG GAA CGC CCG GCA GAT GTG TCC CCA ACA TCC CCA CAG CCC GAG    2633
GGC CTC CTT GTC CTG CAG CAA GTG GGC GAC TAT TGC TTC CTC CCC GGC    2681
CTG GGG CCC GGC CCT CTC TCG CTC CGG AGT AAA CCT TCT TCC CCG GGA    2729
CCC GGT CCT GAG ATC AAG AAC CTA GAC CAG GCT TTT CAA GTC AAG AAG    2777
CCC CCA GGC CAG GCT GTG CCC CAG GTG CCC GTC ATT CAG CTC TTC AAA    2825
GCC CTG AAG CAG CAG GAC TAC CTG TCT CTG CCC CCT TGG GAG GTC AAC    2873
AAG CCT GGG GAG GTG TGT TGA GACC CCCAGGCCTA GACAGGCAAG GGGATGGAGA  2928
GGGCTTGCCT TCCCTCCCGC CTGACCTTCC TCAGTCATTT CTGCAAAGCC AAGGGCAGC   2988
CTCCTGTCAA GGTAGCTAGA GGCCTGGGAA AGGAGATAGC CTTGCTCCGG CCCCCTTGAC  3048
CTTCAGCAAA TCACTTCTCT CCCTGCGCTC ACACAGACAC ACACACACAC ACGTACATGC  3108
ACACATTTTT CCTGTCAGGT TAACTTATTT GTAGGTCTG CATTATTAGA ACTTTCTAGA   3168
TATACTCATT CCATCTCCCC CTCATTTTTT TAATCAGGTT TCCTTGCTTT TGCCATTTTT  3228
CTTCCTTCTT TTTTCACTGA TTTATTATGA GAGTGGGGCT GAGGTCTGAG CTGAGCCTTA  3288
TCAGACTGAG ATGCGGCTGG TTGTGTTGAG GACTTGTGTG GGCTGCCTGT CCCCGGCAGT  3348
CGCTGATGCA CATGACATGA TTCTCATCTG GGTGCAGAGG TGGGAGGCAC CAGGTGGGCA  3408
CCCGTGGGGG TTAGGGCTTG GAAGAGTGGC ACAGGACTGG GCACGCTCAG TGAGGCTCAG  3468
GGAATTC                                                            3475
```

( 2 ) INFORMATION FOR SEQ ID NO: 2:

( i ) SEQUENCE CHARACTERISTICS:
        ( A ) LENGTH: 897 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( D ) OTHER INFORMATION: Human GM- CSF receptor; Signal
        Sequence: -17 to -1; Transmembrane domain: 422 to 448;
        potential N-linked glycosylation sites in the
        extracellular domain: 41|14 43; 174|14 176; 329-331

( x i ) SEQUENCE DESCRIPTION: SEQ ID NO: 2:

```
Met  Val  Leu  Ala  Gln  Gly  Leu  Leu  Ser  Met  Ala  Leu  Leu  Ala  Leu
     -15                      -10                      -5
```

| Cys | Trp | Glu | Arg | Ser | Leu | Ala | Gly | Ala | Glu | Glu | Thr | Ile | Pro | Leu |
|---|---|---|---|---|---|---|---|---|---|---|---|---|---|---|
| | | 1 | | | | 5 | | | | 10 | | | | |
| Gln | Thr | Leu | Arg | Cys | Tyr | Asn | Asp | Tyr | Thr | Ser | His | Ile | Thr | Cys |
| | 15 | | | | 20 | | | | | 25 | | | | |
| Arg | Trp | Ala | Asp | Thr | Gln | Asp | Ala | Gln | Arg | Leu | Val | Asn | Val | Thr |
| | 30 | | | | 35 | | | | | 40 | | | | |
| Leu | Ile | Arg | Arg | Val | Asn | Glu | Asp | Leu | Leu | Glu | Pro | Val | Ser | Cys |
| | 45 | | | | 50 | | | | | 55 | | | | |
| Asp | Leu | Ser | Asp | Asp | Met | Pro | Trp | Ser | Ala | Cys | Pro | His | Pro | Arg |
| | 60 | | | | 65 | | | | | 70 | | | | |
| Cys | Val | Pro | Arg | Arg | Cys | Val | Ile | Pro | Cys | Gln | Ser | Phe | Val | Val |
| | 75 | | | | 80 | | | | | 85 | | | | |
| Thr | Asp | Val | Asp | Tyr | Phe | Ser | Phe | Gln | Pro | Asp | Arg | Pro | Leu | Gly |
| | 90 | | | | 95 | | | | | 100 | | | | |
| Thr | Arg | Leu | Thr | Val | Thr | Leu | Thr | Gln | His | Val | Gln | Pro | Pro | Glu |
| | 105 | | | | 110 | | | | | 115 | | | | |
| Pro | Arg | Asp | Leu | Gln | Ile | Ser | Thr | Asp | Gln | Asp | His | Phe | Leu | Leu |
| | 120 | | | | 125 | | | | | 130 | | | | |
| Thr | Trp | Ser | Val | Ala | Leu | Gly | Ser | Pro | Gln | Ser | His | Trp | Leu | Ser |
| | 135 | | | | 140 | | | | | 145 | | | | |
| Pro | Gly | Asp | Leu | Glu | Phe | Glu | Val | Val | Tyr | Lys | Arg | Leu | Gln | Asp |
| | 150 | | | | 155 | | | | | 160 | | | | |
| Ser | Trp | Glu | Asp | Ala | Ala | Ile | Leu | Leu | Ser | Asn | Thr | Ser | Gln | Ala |
| | 165 | | | | 170 | | | | | 175 | | | | |
| Thr | Leu | Gly | Pro | Glu | His | Leu | Met | Pro | Ser | Ser | Thr | Tyr | Val | Ala |
| | 180 | | | | 185 | | | | | 190 | | | | |
| Arg | Val | Arg | Thr | Arg | Leu | Ala | Pro | Gly | Ser | Arg | Leu | Ser | Gly | Arg |
| | 195 | | | | 200 | | | | | 205 | | | | |
| Pro | Ser | Lys | Trp | Ser | Pro | Glu | Val | Cys | Trp | Asp | Ser | Gln | Pro | Gly |
| | 210 | | | | 215 | | | | | 220 | | | | |
| Asp | Glu | Ala | Gln | Pro | Gln | Asn | Leu | Glu | Cys | Phe | Phe | Asp | Gly | Ala |
| | 225 | | | | 230 | | | | | 235 | | | | |
| Ala | Val | Leu | Ser | Cys | Ser | Trp | Glu | Val | Arg | Lys | Glu | Val | Ala | Ser |
| | 240 | | | | 245 | | | | | 250 | | | | |
| Ser | Val | Ser | Phe | Gly | Leu | Phe | Tyr | Lys | Pro | Ser | Pro | Asp | Ala | Gly |
| | 255 | | | | 260 | | | | | 265 | | | | |
| Glu | Glu | Glu | Cys | Ser | Pro | Val | Leu | Arg | Glu | Gly | Leu | Gly | Ser | Leu |
| | 270 | | | | 275 | | | | | 280 | | | | |
| His | Thr | Arg | His | His | Cys | Gln | Ile | Pro | Val | Pro | Asp | Pro | Ala | Thr |
| | 285 | | | | 290 | | | | | 295 | | | | |
| His | Gly | Gln | Tyr | Ile | Val | Ser | Val | Gln | Pro | Arg | Arg | Ala | Glu | Lys |
| | 300 | | | | 305 | | | | | 310 | | | | |
| His | Ile | Lys | Ser | Ser | Val | Asn | Ile | Gln | Met | Ala | Pro | Pro | Ser | Leu |
| | 315 | | | | 320 | | | | | 325 | | | | |
| Asn | Val | Thr | Lys | Asp | Gly | Asp | Ser | Tyr | Ser | Leu | Arg | Trp | Glu | Thr |
| | 330 | | | | 335 | | | | | 340 | | | | |
| Met | Lys | Met | Arg | Tyr | Glu | His | Ile | Asp | His | Thr | Phe | Glu | Ile | Gln |
| | 345 | | | | 350 | | | | | 355 | | | | |
| Tyr | Arg | Lys | Asp | Thr | Ala | Thr | Trp | Lys | Asp | Ser | Lys | Thr | Glu | Thr |
| | 360 | | | | 365 | | | | | 370 | | | | |
| Leu | Gln | Asn | Ala | His | Ser | Met | Ala | Leu | Pro | Ala | Leu | Glu | Pro | Ser |
| | 375 | | | | 380 | | | | | 385 | | | | |
| Thr | Arg | Tyr | Trp | Ala | Arg | Val | Arg | Val | Arg | Thr | Ser | Arg | Thr | Gly |

-continued

|     |     |     |     |     |     |     |     |     |     |     |     |     |     |     |
|-----|-----|-----|-----|-----|-----|-----|-----|-----|-----|-----|-----|-----|-----|-----|
|     |     | 390 |     |     |     | 395 |     |     |     | 400 |     |     |     |     |
| Tyr | Asn | Gly | Ile | Trp | Ser | Glu | Trp | Ser | Glu | Ala | Arg | Ser | Trp | Asp |
|     | 405 |     |     |     |     | 410 |     |     |     | 415 |     |     |     |     |
| Thr | Glu | Ser | Val | Leu | Pro | Met | Trp | Val | Leu | Ala | Leu | Ile | Val | Ile |
|     | 420 |     |     |     |     | 425 |     |     |     | 430 |     |     |     |     |
| Phe | Leu | Thr | Thr | Ala | Val | Leu | Ala | Leu | Arg | Phe | Cys | Gly | Ile |     |
|     | 435 |     |     |     |     | 440 |     |     |     | 445 |     |     |     |     |
| Tyr | Gly | Tyr | Arg | Leu | Arg | Arg | Lys | Trp | Glu | Glu | Lys | Ile | Pro | Asn |
|     | 450 |     |     |     |     | 455 |     |     |     | 460 |     |     |     |     |
| Pro | Ser | Lys | Ser | His | Leu | Phe | Gln | Asn | Gly | Ser | Ala | Glu | Leu | Trp |
|     | 465 |     |     |     |     | 470 |     |     |     | 475 |     |     |     |     |
| Pro | Pro | Gly | Ser | Met | Ser | Ala | Phe | Thr | Ser | Gly | Ser | Pro | Pro | His |
|     | 480 |     |     |     |     | 485 |     |     |     | 490 |     |     |     |     |
| Gln | Gly | Pro | Trp | Gly | Ser | Arg | Phe | Pro | Glu | Leu | Glu | Gly | Val | Phe |
|     | 495 |     |     |     |     | 500 |     |     |     | 505 |     |     |     |     |
| Pro | Val | Gly | Phe | Gly | Asp | Ser | Glu | Val | Ser | Pro | Leu | Thr | Ile | Glu |
|     | 510 |     |     |     |     | 515 |     |     |     | 520 |     |     |     |     |
| Asp | Pro | Lys | His | Val | Cys | Asp | Pro | Pro | Ser | Gly | Pro | Asp | Thr | Thr |
|     | 525 |     |     |     |     | 530 |     |     |     | 535 |     |     |     |     |
| Pro | Ala | Ala | Ser | Asp | Leu | Pro | Thr | Glu | Gln | Pro | Pro | Ser | Pro | Gln |
|     | 540 |     |     |     |     | 545 |     |     |     | 550 |     |     |     |     |
| Pro | Gly | Pro | Pro | Ala | Ala | Ser | His | Thr | Pro | Glu | Lys | Gln | Ala | Ser |
|     | 555 |     |     |     |     | 560 |     |     |     | 565 |     |     |     |     |
| Ser | Phe | Asp | Phe | Asn | Gly | Pro | Tyr | Leu | Gly | Pro | Pro | His | Ser | Arg |
|     | 570 |     |     |     |     | 575 |     |     |     | 580 |     |     |     |     |
| Ser | Leu | Pro | Asp | Ile | Leu | Gly | Gln | Pro | Glu | Pro | Pro | Gln | Glu | Gly |
|     | 585 |     |     |     |     | 590 |     |     |     | 595 |     |     |     |     |
| Gly | Ser | Gln | Lys | Ser | Pro | Pro | Gly | Ser | Leu | Glu | Tyr | Leu | Cys |     |
|     | 600 |     |     |     |     | 605 |     |     |     | 610 |     |     |     |     |
| Leu | Pro | Ala | Gly | Gly | Gln | Val | Gln | Leu | Val | Pro | Leu | Ala | Gln | Ala |
|     | 615 |     |     |     |     | 620 |     |     |     | 625 |     |     |     |     |
| Met | Gly | Pro | Gly | Gln | Ala | Val | Glu | Val | Glu | Arg | Arg | Pro | Ser | Gln |
|     | 630 |     |     |     |     | 635 |     |     |     | 640 |     |     |     |     |
| Gly | Ala | Ala | Gly | Ser | Pro | Ser | Leu | Glu | Ser | Gly | Gly | Gly | Pro | Ala |
|     | 645 |     |     |     |     | 650 |     |     |     | 655 |     |     |     |     |
| Pro | Pro | Ala | Leu | Gly | Pro | Arg | Val | Gly | Gly | Gln | Asp | Gln | Lys | Asp |
|     | 660 |     |     |     |     | 665 |     |     |     | 670 |     |     |     |     |
| Ser | Pro | Val | Ala | Ile | Pro | Met | Ser | Ser | Gly | Asp | Thr | Glu | Asp | Pro |
|     | 675 |     |     |     |     | 680 |     |     |     | 685 |     |     |     |     |
| Gly | Val | Ala | Ser | Gly | Tyr | Val | Ser | Ser | Ala | Asp | Leu | Val | Phe | Thr |
|     | 690 |     |     |     |     | 695 |     |     |     | 700 |     |     |     |     |
| Pro | Asn | Ser | Gly | Ala | Ser | Ser | Val | Ser | Leu | Val | Pro | Ser | Leu | Gly |
|     | 705 |     |     |     |     | 710 |     |     |     | 715 |     |     |     |     |
| Leu | Pro | Ser | Asp | Gln | Thr | Pro | Ser | Leu | Cys | Pro | Gly | Leu | Ala | Ser |
|     | 720 |     |     |     |     | 725 |     |     |     | 730 |     |     |     |     |
| Gly | Pro | Pro | Gly | Ala | Pro | Gly | Pro | Val | Lys | Ser | Gly | Phe | Glu | Gly |
|     | 735 |     |     |     |     | 740 |     |     |     | 745 |     |     |     |     |
| Tyr | Val | Glu | Leu | Pro | Pro | Ile | Glu | Gly | Arg | Ser | Pro | Arg | Ser | Pro |
|     | 750 |     |     |     |     | 755 |     |     |     | 760 |     |     |     |     |
| Arg | Asn | Asn | Pro | Val | Pro | Pro | Glu | Ala | Lys | Ser | Pro | Val | Leu | Asn |
|     | 765 |     |     |     |     | 770 |     |     |     | 775 |     |     |     |     |
| Pro | Gly | Glu | Arg | Pro | Ala | Asp | Val | Ser | Pro | Thr | Ser | Pro | Gln | Pro |
|     | 780 |     |     |     |     | 785 |     |     |     | 790 |     |     |     |     |

-continued

| | | | | | | | | | | | | | |
|---|---|---|---|---|---|---|---|---|---|---|---|---|---|
| Glu | Gly 795 | Leu | Leu | Val | Leu | Gln 800 | Gln | Val | Gly | Asp | Tyr 805 | Cys | Phe Leu |
| Pro | Gly 810 | Leu | Gly | Pro | Gly | Pro 815 | Leu | Ser | Leu | Arg | Ser 820 | Lys | Pro Ser |
| Ser | Pro 825 | Gly | Pro | Gly | Pro | Glu 830 | Ile | Lys | Asn | Leu | Asp 835 | Gln | Ala Phe |
| Gln | Val 840 | Lys | Lys | Pro | Pro | Gly 845 | Gln | Ala | Val | Pro | Gln 850 | Val | Pro Val |
| Ile | Gln 855 | Leu | Phe | Lys | Ala | Leu 860 | Lys | Gln | Gln | Asp | Tyr 865 | Leu | Ser Leu |
| Pro | Pro 870 | Trp | Glu | Val | Asn | Lys 875 | Pro | Gly | Glu | Val | Cys 880 | | |